(12) United States Patent
Radisch, Jr.

(10) Patent No.: US 6,632,231 B2
(45) Date of Patent: Oct. 14, 2003

(54) SEGMENTED BALLOON CATHETER BLADE

(75) Inventor: Herbert R. Radisch, Jr., San Diego, CA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 22 days.

(21) Appl. No.: 09/938,010

(22) Filed: Aug. 23, 2001

(65) Prior Publication Data

US 2003/0040770 A1 Feb. 27, 2003

(51) Int. Cl.[7] .............................................. A61B 17/08
(52) U.S. Cl. .................................... 606/159; 606/194
(58) Field of Search ............................ 606/159, 167, 606/170, 191, 192, 194

(56) References Cited

U.S. PATENT DOCUMENTS

| | | | |
|---|---|---|---|
| 2,730,101 A | 1/1956 | Hoffman | |
| 3,512,519 A | 5/1970 | Hall | |
| 3,605,721 A | 9/1971 | Hallac | |
| 4,273,128 A | 6/1981 | Lary | |
| 4,669,469 A | 6/1987 | Gifford | |
| 4,886,061 A | * 12/1989 | Fischell et al. | 606/159 |
| 4,966,604 A | 10/1990 | Reiss | |
| 5,074,841 A | * 12/1991 | Ademovic et al. | 606/159 |
| 5,196,024 A | 3/1993 | Barath | |
| 5,320,634 A | * 6/1994 | Vigil et al. | 606/159 |
| 5,336,234 A | * 8/1994 | Vigil et al. | 606/159 |
| 5,616,149 A | * 4/1997 | Barath | 606/159 |
| 5,746,716 A | * 5/1998 | Vigil et al. | 606/194 |
| 5,792,158 A | * 8/1998 | Lary | 606/159 |
| 5,797,935 A | 8/1998 | Barath | |
| 6,258,108 B1 | * 7/2001 | Lary | 606/194 |
| 6,319,242 B1 | * 11/2001 | Patterson et al. | 606/159 |
| 2002/0010489 A1 | * 1/2002 | Grayzel et al. | 606/194 |

* cited by examiner

Primary Examiner—Michael J. Milano
Assistant Examiner—Jessica R Baxter
(74) Attorney, Agent, or Firm—Nydegger & Associates

(57) ABSTRACT

A device for incising a stenosis in the vasculature of a patient includes a plurality of blades mounted on a resilient base member. The blades are arranged in a pattern to allow for relative movement between adjacent blades. Specifically, at least one end portion of each blade is juxtaposed with an end portion of the next closest blade. The base member, in turn, is mounted on the external surface of an inflatable angioplasty balloon. When the balloon is inserted into the vasculature of a patient, positioned across a stenosis and subsequently inflated, the individually moveable blades form an effective cutting edge that conforms to the surface of the stenosis to effectively allow the stenosis to be incised to a substantially uniform depth.

12 Claims, 2 Drawing Sheets

SEGMENTED BALLOON CATHETER BLADE

FIELD OF THE INVENTION

The present invention relates generally to medical devices. More particularly, the present invention pertains to invasive surgical devices which are useful for the incision and dilation of a stenosis in the vasculature of a patient. The present invention is particularly, though not exclusively, useful for incising a stenosis with a balloon catheter blade to facilitate subsequent dilation of the stenosis.

BACKGROUND OF THE INVENTION

The blockage of human arteries can lead to a variety of serious medical complications. This is so because arterial blockages reduce blood flow through the affected artery and may result in damage to the tissue that is relying on the blood supply. For example, if the blockage is in an artery which supplies blood to the heart itself, a heart attack may result.

Such arterial blockages, which are also called stenoses, are typically caused by the build-up of atherosclerotic plaque on the inside wall of an artery. In fact, several such stenoses may occur contiguously within a single artery. This can result in a partial, or even complete, blockage of the artery. As a result of the danger associated with such a blockage, several methods and procedures have been developed to treat stenoses. One such method is an angioplasty procedure which uses an inflatable balloon to dilate the blocked artery. A typical inflatable angioplasty device, for example, is disclosed in U.S. Pat. No. 4,896,669 which issued to Bhate et al. for an invention entitled "DILATION CATHETER". The Bhate et al. angioplasty device includes an inflatable angioplasty balloon which is insertable into a peripheral artery of a patient for positioning across a stenosis. Once positioned, the angioplasty balloon is then inflated to flatten the stenosis against the inside wall of the artery thereby improving the blood flow through the artery.

Angioplasty balloons have enjoyed widespread acceptance in the treatment of stenoses. Recent studies, however, have indicated that the efficacy of the dilation of a stenosis is enhanced by first, or simultaneously, incising the material that is creating the stenosis. Consequently, recent developments have been made to equip angioplasty balloons with cutting edges, or atherotomes, which are intended to incise a stenosis during the dilation procedure. For example, the device disclosed in U.S. Pat. No. 5,196,024 to Barath entitled "BALLOON CATHETER WITH CUTTING EDGE," which is assigned to the assignee of the present invention, is an inflatable angioplasty balloon having a number of atherotomes mounted longitudinally on the surface of the balloon.

Upon inflation of the Barath balloon, the atherotomes induce a series of longitudinal cuts into the surface of the stenotic material as the balloon expands to dilate the stenosis. As a result of such cuts, the stenosis is more easily flattened, and the likelihood of damaging the artery during dilation is reduced. Generally, however, the surface of a stenosis is bumpy and undulating, and contains numerous peaks and valleys. As such, incision of a stenosis with one long, continuous blade that is mounted on the surface of an angioplasty balloon can be uneven. Specifically, while the peaks of a stenotic surface may be effectively incised, incisions in the valleys present on the surface of the stenosis may be problematic. Thus, it can happen that only a small portion of the stenosis is actually incised. Furthermore, long, continuous blades reduce the flexibility of the catheter making it more difficult to guide the catheter through the vasculature of the patient.

In light of the above, it is an object of the present invention to provide a device for incising both the peaks and valleys of a stenosis in a vessel of a patient. It is a further object of the present invention to provide a blade unit for an angioplasty balloon having an effective cutting edge that substantially conforms to the surface of a stenosis when the balloon is inflated. It is still another object of the present invention to provide a device for incising a stenosis that is flexible enough to be easily guided through the vasculature of the patient to the site of the stenosis. It is another object of the present invention to provide a device for incising a stenosis in a vessel which is relatively simple to manufacture, is easy to use, and is comparatively cost effective.

SUMMARY OF THE PREFERRED EMBODIMENTS

For the present invention, a device for incising a stenosis in the vasculature of a patient includes a plurality of blade segments that are mounted and aligned on a base member. The base member, in turn, is mounted on the external surface of an inflatable angioplasty balloon. Accordingly, when the balloon is inserted into the vasculature of a patient, positioned across a stenosis and subsequently inflated, the blade segments form an effective cutting edge that effectively conforms to the surface of the stenosis. Due to this ability of the cutting edge to conform with the peaks and valleys of the stenosis, the stenosis can be incised to a substantially uniform depth.

In detail, to establish an effective cutting edge conformable to the surface of a stenosis, the blade segments are attached to the base member in a pattern that allows relative movement between adjacent blade segments. For the present invention, each individual blade segment is generally elongated and defines a blade axis in the direction of its elongation. Preferably, each blade segment is mounted on the base member and oriented with its blade axis either substantially parallel or substantially colinear with the blade axis of at least one other blade segment. Further, the distal portion of each blade segment is juxtaposed and preferably in contact with the proximal portion of the next closest blade segment (except for the blade segment at the extreme distal end of the pattern). As such, each blade segment is off-set from the next closest blade segment in the axial direction.

For the present invention, the base member is made of a resilient material, such as a thin strip of polyurethane material, which allows the base member to deform along with the surface of the angioplasty balloon during an inflation or deflation of the balloon. One side of the base member is preferably bonded to the external surface of the angioplasty balloon. For the present invention, an elongated angioplasty balloon, defining a balloon axis in the direction of elongation, is generally used. Preferably, the base member is also elongated and is mounted on the external surface of the balloon with the direction of base member elongation parallel to the balloon axis. For the present invention, the blade segments are mounted on the base member with each blade axis substantially parallel to the direction of base member elongation. Furthermore, each blade segment is formed with a taper section that creates a sharpened edge. Preferably, each blade segment is oriented on the base member with the sharpened edge of each blade segment lying substantially along a single continuous cutting line.

In operation, a catheter having an angioplasty balloon, base member and blade segments is inserted into the vasculature of a patient. The catheter is then advanced within the vasculature until the angioplasty balloon is positioned across a stenosis requiring treatment. For this purpose, a guidewire can be used to establish a mechanical pathway to assist the catheter to the treatment site. Next, the balloon is slowly inflated causing the external surface of the balloon, the base member and the blade segments to move outwardly together in a radial direction from the balloon axis until the blade segments contact the surface of the stenosis.

Upon contact with the surface of the stenosis, the sharpened edge of each blade segment cuts into the stenosis, creating an incision. Inflation of the balloon is then continued until the blade segments are effectively embedded into the stenosis. Eventually, the external surface of the balloon and the resilient base member contact and conform with the surface of the stenosis. Because the blades are segmented and positioned on the base member to allow relative movement between blade segments, the blade segments do not prevent the balloon and base member from conforming to the surface of the stenosis. Additionally, the relative movement between the blade segments allows the blade segments to form an effective cutting edge that conforms to the surface of the stenosis resulting in a nearly continuous incision of substantially uniform depth along the surface peaks and valleys of the stenosis.

After incision, the angioplasty balloon can be further inflated to dilate the stenosis, if desired. In any case, the angioplasty balloon is subsequently deflated to withdraw the blade segments from the stenosis. Once deflated, the balloon and blade segments can be repositioned for treatment of another stenosis or removed from the patient.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENT

Figure 1:
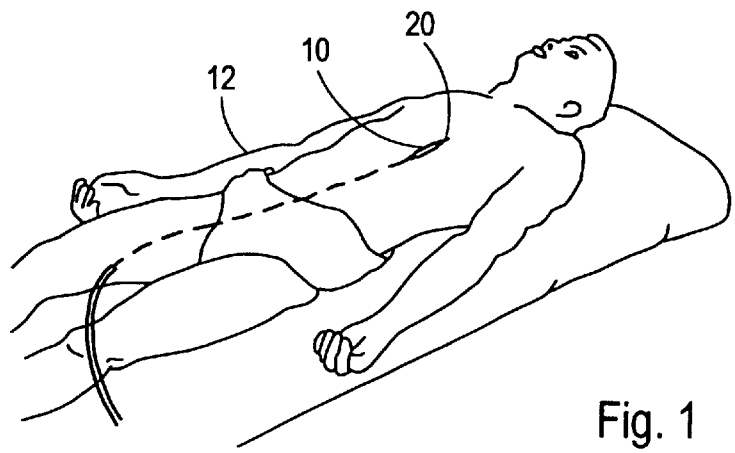
FIG. 1 is a perspective view of a patient with a device in accordance with the present invention positioned in an artery to allow for the incision of a stenosis.
Figure 2:
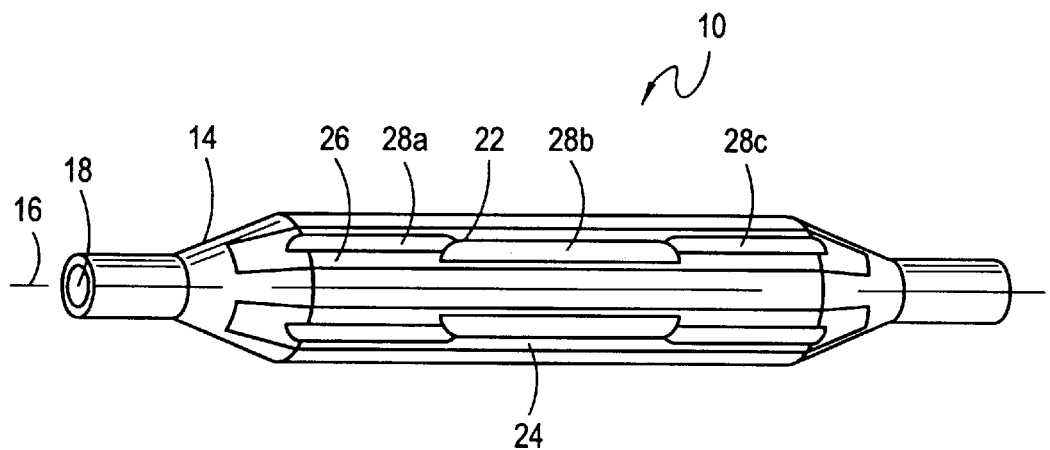
FIG. 2 is an enlarged perspective view of a balloon catheter having segmented blades in accordance with the present invention (balloon shown in inflated configuration)

Referring initially to FIG. 1, a device 10 for incising and dilating a stenosis is shown positioned for operation inside a patient 12. As shown in FIG. 2, the device 10 includes an angioplasty balloon 14 that is elongated and defines a balloon axis 16. As shown, lumen 18 is provided to allow the balloon 14 to be tracked along a guidewire 20 (shown in FIG. 1) and to allow for inflation/deflation of the balloon 14. For the present invention, one or more blade units such as blade unit 22 and blade unit 24 are mounted on the external surface of the angioplasty balloon 14.

Figure 3:
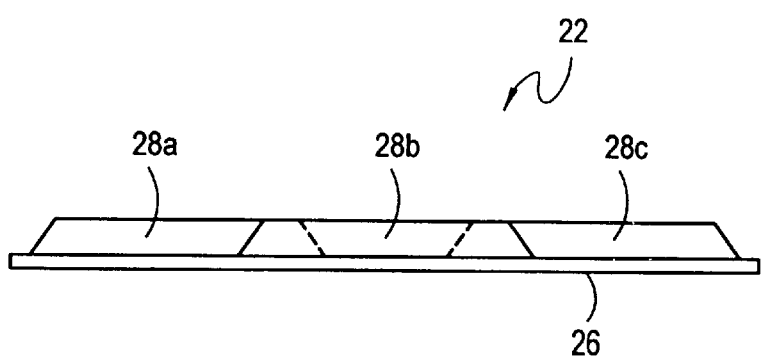
FIG. 3 is an enlarged elevation view of a blade unit having three segmented blades mounted on a base member (dotted lines are provided to show portions of the two outer blades that are behind the center blade for clarity)
Figure 4:
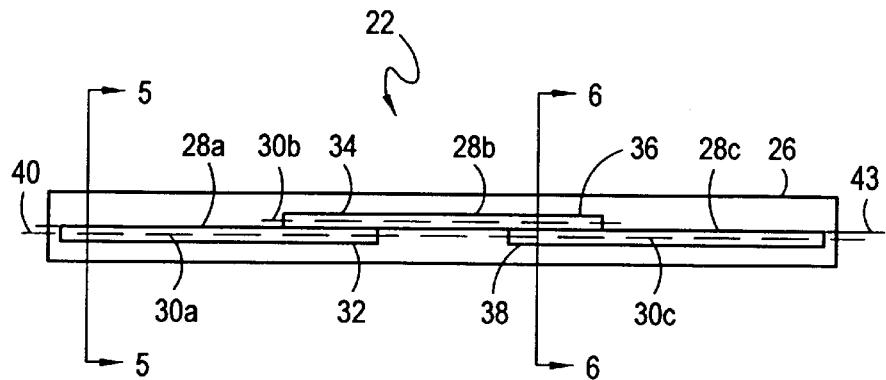
FIG. 4 is an enlarged plan view of a blade unit having three segmented blades mounted on a base member.

Referring now with cross reference to FIGS. 2, 3 and 4, it is to be appreciated that the blade unit 22 includes a base member 26 and a plurality of blade segments 28a, 28b and 28c. Although only three blade segments 28a, 28b, 28c are shown, it is to be appreciated that a blade unit 22 can contain any number of blade segments 28a, 28b, 28c for the present invention. Preferably, each blade segment 28a, 28b, 28c is made of a hard, biocompatible material such as stainless steel.

As shown, each blade segment 28a, 28b, 28c is generally elongated and defines a blade axis 30 in the direction of elongation. In the preferred embodiment, each blade segment 28a, 28b, 28c is mounted on the base member 26 and oriented with its blade axis 30a, 30b, 30c either substantially parallel or substantially colinear with the blade axis 30a, 30b, 30c of at least one other blade segment 28a, 28b, 28c. Attachment of the blade segments 28a, 28b, 28c to the base member 26 can be accomplished using any method known in the pertinent art such as bonding pre-formed blade segments 28a, 28b, 28c to the base member 26 with an adhesive.

Referring now to FIG. 4, it can be seen that the blade segments 28a, 28b, 28c are arranged on the base member 26 in a pattern to allow each blade segment 28a, 28b, 28c to move independently of the other blade segments 28a, 28b, 28c. Specifically, as shown and identifying a distal direction to the right and a proximal direction to the left in FIG. 4, the distal portion 32 of blade segment 28a is juxtaposed with the proximal portion 34 of blade segment 28b. Similarly, the distal portion 36 of blade segment 28b is juxtaposed with the proximal portion 38 of blade segment 28c. Preferably, as shown, every other blade segment 28a, 28b, 28c along the pattern, such as blade segments 28a and 28c, are aligned parallel to a common axis, such as axis 40. Further, as shown, blade segment 28b is off-set from blade segment 28a and blade segment 28c in the direction of axis 40. For the present invention, the size and shape of each blade segment 28a, 28b, 28c, the amount of the off-set, and the extent of the portions that are juxtaposed can be varied depending on the particular application.

Figure 5:
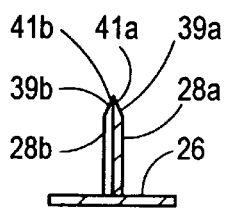
FIG. 5 is a sectional view of the blade unit as seen along line 5—5 in FIG. 4.
Figure 6:
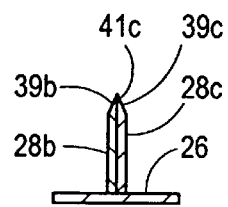
FIG. 6 is a sectional view of the blade unit as seen along line 6—6 in FIG. 4.

As shown in FIG. 5, blade segment 28a is formed with a tapered section 39 that creates a sharpened edge 41 of the blade segment 28a. By cross referencing FIGS. 4, 5 and 6, it can be appreciated that the tapered section 39a, 39b, 39c of each respective blade segment 28a, 28b and 28c preferably inclines toward a cutting line 43. As such, the sharpened edge 41a, 41b, 41c of each blade segment 28a, 28b, 28c preferably lies substantially along the cutting line 43.

Importantly, the base member 26 is made of a resilient material, such as a thin strip of polyurethane material, allowing the base member 26 to deform along with the angioplasty balloon 14 during inflation, deflation and contact with the stenosis. As shown in FIG. 2, one side of the base member 26 is preferably bonded to the external surface of the angioplasty balloon 14. Also shown, the base member 26 is preferably elongated and is mounted on the external surface of the balloon 14 with the direction of elongation of the base member 26 parallel to the balloon axis 16.

Accordingly, the blade segments 28a, 28b, 28c are aligned substantially parallel to the balloon axis 16.

Figure 7:
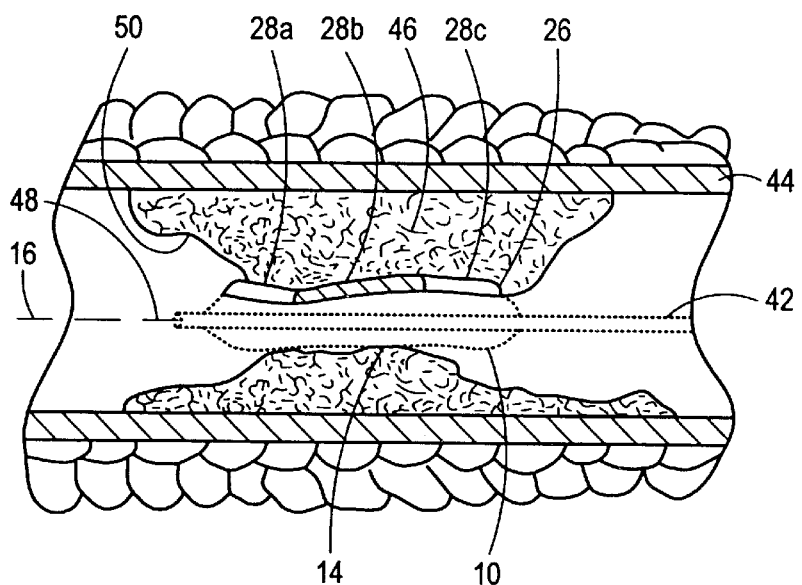
FIG. 7 is a cross-sectional view of a balloon catheter having segmented blades positioned across a stenosis in the vessel of a patient and inflated to embed the blades into the stenosis.

The operation of the device 10 can be best appreciated with reference to FIG. 7. A catheter 42 having a device 10 that includes an angioplasty balloon 14, base member 26 and blade segments 28a, 28b, 28c is first inserted into a vessel 44 of a patient 12. To treat a stenosis 46, the catheter 42 is advanced in the vessel 44 until the angioplasty balloon 14 is positioned across the stenosis 46. As shown, a guidewire 48 can be used to establish a mechanical pathway to assist the catheter 42 to the treatment site. Once properly positioned, the balloon 14 is slowly inflated causing the external surface of the balloon 14, the base member 26 and the blade segments 28a, 28b, 28c to move outwardly in a radial direction from the balloon axis 16 until the blade segments 28a, 28b, 28c contact the surface 50 of the stenosis 46.

Referring still to FIG. 7, it is to be appreciated that inflation of the balloon 14 will cause one or more of the blade segments 28a, 28b, 28c to contact the surface 50 of the stenosis 46 and cut an incision in the stenosis 46. Continued inflation of the balloon 14 causes one or more blade segments 28a, 28b, 28c to embed into the stenosis 46. Eventually, the external surface of the balloon 14 and the resilient base member 26 contact and conform with the surface 50 of the stenosis 46. Because of the articulation and offset of the blade segments 28a, 28b, 28c, the blade segments 28a, 28b, 28c are able to move independently and the blade segments 28a, 28b, 28c do not prevent the balloon 14 and base member 26 from conforming to the surface 50 of the stenosis 46. Additionally, as shown, the relative movement between the blade segments 28a, 28b, 28c allows the blade segments 28a, 28b, 28c to form an effective cutting edge along the cutting line 43 (shown in FIG. 4) that conforms to the surface 50 of the stenosis 46 resulting in a nearly continuous incision of substantially uniform depth along the surface peaks and valleys of the stenosis 46.

After incision, the angioplasty balloon 14 can be further inflated to dilate the stenosis 46, if desired. After treatment, the angioplasty balloon 14 is subsequently deflated, withdrawing the blade segments 28a, 28b, 28c from the stenosis 46. Once deflated, the balloon 14 can be re-inflated to repeat the process, if desired. After treatment of the stenosis 46, the deflated balloon 14 can be repositioned for treatment of another stenosis 46 or removed from the patient 12.

While the particular devices and methods as herein shown and disclosed in detail are fully capable of obtaining the objects and providing the advantages herein before stated, it is to be understood that they are merely illustrative of the presently preferred embodiments of the invention and that no limitations are intended to the details of construction or design herein shown other than as described in the appended claims.

What is claimed is:

1. An apparatus for use in performing an angioplasty procedure at the site of a stenosis in the vasculature of a patient which comprises:

an inflatable balloon, said inflatable balloon defining an axis, having an external surface and being insertable into the vasculature of a patient for movement therein between a deflated configuration and an inflated configuration;

a resilient base member mounted on said external surface of said balloon, said base member being substantially compliant with said external surface of said balloon during movement therewith; and a plurality of blade segments attached to said base member, with a portion of each said blade segment being juxtaposed with a portion of at least one other said blade segment and being axially off-set therefrom to allow relative movement therebetween during a movement of said balloon from said deflated configuration into said inflated configuration to embed at least one of said plurality of blade segments into the stenosis while said external surface of said balloon conforms with the stenosis and the vasculature of the patient.

2. An apparatus as recited in claim 1 wherein said balloon is elongated and further wherein said base member is mounted on said external surface of said balloon in a substantially axial orientation.

3. An apparatus as recited in claim 1 wherein said base member is made of a polyurethane material.

4. An apparatus as recited in claim 1 wherein said plurality of blade segments mounted on said base member are a blade unit and further wherein said apparatus comprises a plurality of said blade units.

5. An apparatus as recited in claim 1 wherein each said blade segment is made of stainless steel.

6. An apparatus as recited in claim 1 wherein said apparatus comprises at least three said blade segments.

7. An apparatus as recited in claim 1 wherein each said blade segment is elongated defining a blade axis for each said blade segment, and each said blade segment is mounted on said balloon with its blade axis substantially parallel to said axis of said balloon.

8. A method for incising a stenosis in the vasculature of a patient, said method comprising:

inserting a catheter in the vasculature, said catheter having an inflatable balloon that defines an axis and is formed with an external surface, a resilient base member mounted on said external surface of said balloon, said base member being substantially compliant with said external surface of said balloon during movement therewith, and a plurality of blade segments attached to said base member, with a portion of each said blade segment being juxtaposed with a portion of at least one other said blade segment and being axially off-set therefrom;

advancing said catheter within the vasculature until the inflatable balloon is across the stenosis; and inflating the balloon to cause at least one of said plurality of blade segments to move relative to the other said blade segments and to embed at least one of said plurality of blade segments into the stenosis and allow said external surface of said balloon to conform to the stenosis.

9. A method as recited in claim 8 wherein said advancing step comprises the steps of:

inserting a guidewire in the vasculature of the patient; and tracking said guidewire with said catheter to position said inflatable balloon across the stenosis.

10. A method as recited in claim 8 further comprising the step of deflating said balloon to withdraw said blade segments from said stenosis.

11. A method as recited in claim 8 wherein said inflating step is conducted to incise and dilate the stenosis.

12. A method as recited in claim 8 further comprising the step of removing said balloon and said blade segments from the patient.

* * * * *